(12) United States Patent
Régnier

(10) Patent No.: US 10,099,060 B2
(45) Date of Patent: Oct. 16, 2018

(54) HYBRID SYSTEM FORMING AN ACTIVE IMPLANTABLE MEDICAL DEVICE

(71) Applicant: SORIN CRM SAS, Clamart (FR)

(72) Inventor: Willy Régnier, Longjumeau (FR)

(73) Assignee: Sorin CRM SAS, Clamart (FR)

( * ) Notice: Subject to any disclaimer, the term of this patent is extended or adjusted under 35 U.S.C. 154(b) by 325 days.

(21) Appl. No.: 14/744,991

(22) Filed: Jun. 19, 2015

(65) Prior Publication Data

US 2016/0008612 A1    Jan. 14, 2016

(30) Foreign Application Priority Data

Jun. 25, 2014 (FR) ..................................... 14 55899

(51) Int. Cl.
*A61N 1/372* (2006.01)
*A61N 1/375* (2006.01)
(Continued)

(52) U.S. Cl.
CPC ........ *A61N 1/37288* (2013.01); *A61B 5/0028* (2013.01); *A61B 5/076* (2013.01); *A61B 5/6869* (2013.01); *A61N 1/368* (2013.01); *A61N 1/3756* (2013.01); *A61N 1/37205* (2013.01); *A61N 1/37217* (2013.01); *A61N 1/37282* (2013.01); *A61B 5/0015* (2013.01); *A61B 5/6882* (2013.01)

(58) Field of Classification Search
None
See application file for complete search history.

(56) References Cited

U.S. PATENT DOCUMENTS

| 4,932,409 A * | 6/1990 | Hirschberg .......... A61N 1/3752 607/36 |
| 6,409,674 B1 | 6/2002 | Brockway et al. |

(Continued)

FOREIGN PATENT DOCUMENTS

| EP | 2 394 695 A1 | 12/2011 |
| EP | 2 441 491 A1 | 4/2012 |

(Continued)

OTHER PUBLICATIONS

Preliminary Search Report for French Patent Application No. FR 1455899, dated Feb. 25, 2015, 1 page.

*Primary Examiner* — Brian T Gedeon
(74) *Attorney, Agent, or Firm* — Foley & Lardner LLP

(57) ABSTRACT

A hybrid system forming an active implantable medical device includes a subcutaneous autonomous capsule and at least one intracorporeal autonomous leadless capsule. The subcutaneous capsule is a hybrid capsule having a seal body of dimensions comparable to those of a leadless capsule, but extended by a detection/stimulation microlead, without any intermediate connector. The leadless capsule includes a seal body, anchoring means in a wall of an organ and a detection/stimulation electrode. The hybrid capsule and the leadless capsules each include transmitter/receiver means for intracorporeal mutual wireless communication so as to constitute a network wherein the hybrid capsule is the master and leadless capsules are the slaves. The hybrid capsule further includes means for centralizing data transmitted by the leadless capsules and for exchanging data with remote external equipment.

19 Claims, 2 Drawing Sheets

(51) Int. Cl.
    *A61N 1/368*    (2006.01)
    *A61B 5/00*     (2006.01)
    *A61B 5/07*     (2006.01)

(56)         References Cited

U.S. PATENT DOCUMENTS 7,634,313  B1    12/2009  Kroll et al.
    7,734,343  B2 *   6/2010  Ransbury .............. A61N 1/05
                                                          606/129
    7,899,554  B2 *   3/2011  Williams ............ A61N 1/057
                                                          607/126
    7,945,325  B2 *   5/2011  Stahmann .......... A61N 1/3622
                                                           607/15
    8,311,633  B2 *  11/2012  Ransbury .............. A61F 2/95
                                                           607/36
    8,554,336  B2 *  10/2013  Bly ................... A61N 1/056
                                                          607/116
    8,644,934  B2 *   2/2014  Hastings ............. A61N 1/372
                                                           607/32
    9,248,271  B2 *   2/2016  Regnier ................ A61N 1/05
    9,265,864  B2 *   2/2016  Regnier .............. A61N 1/056
    9,585,642  B2 *   3/2017  Dinsmoor .......... A61N 1/36139
    9,623,234  B2 *   4/2017  Anderson ............ A61N 1/056
    2012/0109258 A1* 5/2012  Cinbis ................ A61B 5/0028
                                                           607/60
    2012/0130464 A1* 5/2012  Ollivier .............. A61N 1/056
                                                          607/122
    2017/0189681 A1* 7/2017  Anderson .......... A61N 1/3684

FOREIGN PATENT DOCUMENTS

EP        2 486 953 A1    8/2012
    EP        2 581 107 A1    4/2013
    EP        2 638 930 A1    9/2013
    EP        2 639 845 A1    9/2013
    EP        2 682 151 A1    1/2014
    EP        2 719 422 A1    4/2014

* cited by examiner

HYBRID SYSTEM FORMING AN ACTIVE IMPLANTABLE MEDICAL DEVICE

CROSS-REFERENCE TO RELATED PATENT APPLICATIONS

This application claims the benefit of and priority to French Patent Application No. 1455899, filed Jun. 25, 2014, which is hereby incorporated by reference herein in its entirety.

BACKGROUND

The invention relates to "active implantable medical devices" as defined by Directive 90/385/EEC of 20 Jun. 1990 of the Council of the European Communities, specifically the detection of electrical potentials generated by organs and/or electrical stimulation of these organs, in particular cardiac diagnostic and therapy applications.

However, although in the following mainly a cardiac detection/stimulation system is described, this application is not limitative of the invention which, as will be understood, may also be applied, mutatis mutandis, to the detection/stimulation of other organs such as the nervous system (including brain stimulation or nerve stimulation), the arterial or lymphatic system, the digestive system (stomach, intestine) or the respiratory system.

In the case of the heart, the invention relates more particularly to the situation of patients with Heart Failure (HF), to which the implantation of a cardiac resynchronization device of the CRT-P type (pacemaker) or CRT-D type (pacemaker with also defibrillator function) is proposed.

The therapy aims to resynchronize the contraction of both ventricles between them, and if necessary one of the ventricles relative to the atrium in order to improve the patient's condition by optimizing the phases of the hemodynamic cycle. For this, the devices implement a technique called "CRT" (Cardiac Resynchronization Therapy) or "BVP" (Bi-Ventricular Pacing) of issuing as necessary electrical pulses ensuring joint and permanent stimulation of both the left and right ventricles to resynchronize the contractions of the latter.

Regarding the implanted device, it requires the implantation in the right ventricle of a conventional endocardial pacing lead and for the stimulation of the left ventricle of a lead inserted into the coronary venous system CVS via the coronary sinus, so as to place the pacing electrode of this lead against the wall of the left ventricle. An alternative is to use an epicardial lead as the left ventricular lead, introduced into the pericardial sac and secured to the outer wall of the heart muscle. The device also often provides the implementation of a third lead positioned in the right atrial cavity, for detecting the contraction of the atrium in order to synchronize on it the stimulation of the ventricles, by respecting the chronology of the atrioventricular delay.

These endocardial or coronary leads are introduced through the patient's venous system, which can lead to complications such as displacement, insulation or conductor breakage, fibrosis development, etc.

To reduce these risks, a new generation of devices has been developed, which are in the form of implantable autonomous capsules in a heart chamber (ventricle, left atrium or even arterial left cardiac chamber) and are generally referred to as "leadless capsules." These capsules are devoid of any physical connection to a main implantable device (such as the housing of a stimulation pulse generator) or non implantable device (external device such as a programmer or a monitoring device for patient remote monitoring). They are qualified for this reason as leadless, to distinguish them from the electrodes disposed at the distal end of a conventional lead (lead), crossed along its entire length by one or more conductors galvanically connecting the distal electrode to a connector located at the opposite, proximal end of the lead, the connector being intended to be connected to the housing of the pulse generator.

These leadless capsules can advantageously replace conventional endocardial leads such as right ventricular and right atrial leads, or the epicardial leads, but because of their size they cannot be substituted for the stimulation of the left ventricle to leads introduced into the coronary venous system, leads which are required for detection/stimulation of the left ventricle, therefore the application of a CRT therapy. In addition, the endocardial arterial network (thus providing access to the left cavities) remains extremely risky, even with a leadless capsule, because of the serious risk of bleeding or blood clots, which can form arterial emboli.

On the other hand, with regards to the left coronary leads, the need for a guidewire to be used for implantation, the standard norm of the multipolar left lead connectors (IS-4 or DF-4 standards) and the need for a central lumen formed in the lead body for the introduction of the guidewire, are constraints that limit the ability to reduce the diameter of the coronary leads and therefore to reach new target areas of stimulation of the left ventricle that remain difficult to reach today.

U.S. Pat. No. 7,634,313 B1 describes a biventricular pacing system combining:

For stimulation of the right ventricle, a conventional pacemaker with a generator housing connected to an also conventional endocardial lead, and For stimulation of the left ventricle, an epicardial leadless capsule implanted on the outer wall of the left ventricle and communicating by wireless link with the generator, the latter playing a role of the master and the leadless capsule that of the satellite.

With this system, however, the problems mentioned above remain, as well as those specific to conventional pacemakers (generator volume, difficulty reaching the coronary sinus with the lead, implantation with guidewire delivery system, etc.) and, finally, need for intervention by transthoracic approach for implantation of the epicardial capsule.

The aim of the invention is to propose a device that overcomes the various drawbacks exposed above.

SUMMARY

The present invention forms an assembly including first, a device that will be described in the following as "hybrid capsule" for the detection/stimulation of the left ventricle and, second, of leadless capsules for detection/stimulation of the right cavities (right ventricle and, if necessary, right atrium).

"Hybrid capsule" should be understood to mean a device:
Made of a body having the same shape and same configuration as that of a leadless capsule with a low-power electronic architecture, a miniaturized energy source and capable of wireless communication with other capsules,
Wherein this body is provided with a lead extending away from the body of capsule without solution of continuity (that is to say without intermediate connector) so as to form an integral and fully autonomous device, This lead furthermore being a "microlead," that is to say, a miniaturized lead of very small diameter (typically not more than 1 French or 0.33 mm) and free of internal lumen, formed of a core cable coated with an insulation layer with, in the distal region, one or more selectively exposed areas forming some detection/stimulation electrodes.

More precisely, one embodiment of the invention includes, with reference to U.S. Pat. No. 7,634,313 B1 above:

A subcutaneous autonomous unit including a sealed housing electronic circuits and electrical power supply methods for these electronic circuits; and extending said body, at least one lead for detection and/or therapy delivery, such lead including at least one sensing and/or therapy delivery electrode; and At least one autonomous leadless intracorporeal capsule adapted to be implanted in or against a body and including: a seal body accommodating electronic circuits and electrical power supply methods for these circuits; methods for anchoring to a wall of said body; and at least one sensing and/or therapy delivery electrode capable of coming into direct contact with said member.

The autonomous unit and the leadless capsule each include intracorporeal mutual wireless transmission/reception communication methods, the independent unit operating as a master and the leadless capsule(s) operating as slaves under the control of the master autonomous unit.

The autonomous unit also includes methods of centralization of data transmitted by the leadless capsules, and methods of communication with the outside, able to operate a remote transmission to a remote device, of the data collected by the methods of centralization of data.

According to an exemplary embodiment of the invention:

The at least one detection and/or therapy delivery lead is a microlead including at least one microcable formed of an electrically conductive core cable connected to one pole of said electronic circuits with an insulation layer surrounding the core cable and including at least one selectively exposed area formed in the insulating layer, and for forming said sensing and/or therapy delivery electrode, the diameter of the microlead being at most 1 French (0.33 mm) in its distal region comprising said selectively exposed area; and The autonomous unit is a hybrid capsule having a volume of at most 1 cm$^3$ and wherein the hybrid capsule is devoid of electrical connector between the microlead and the electronic circuits, the at least one microlead extends from said body on one side thereof, and the core cable of the microcable or each microcable is directly connected to a respective pole of the electronic circuits of the hybrid capsule.

According to various advantageous embodiments:

The hybrid capsule is free of anchoring methods in a wall of an organ;

The seal body of the hybrid capsule is a metal body including at least a hermetic and electrically insulating bushing for the passage of the connection of the core cable of the microcable or of each core cable of each microcable, the respective pole electronic circuits contained in the body of the hybrid capsule;

The capsule supports, at the opposite side of the side extended by the microlead, a transmission/reception antenna for wireless communication with said remote device; and The at least one detection and/or therapy delivery microlead includes, in the proximal region of the microlead attached to the body of the hybrid capsule, a transition region of variable gradient stiffness, decreasing in the distal direction.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

We will now describe an embodiment of the invention, applied to a cardiac resynchronizer system (CRT).

As explained in the introduction, this example is only illustrative, the invention being possibly implemented in the context of very different detection/stimulation configurations, especially in a context that is not necessarily related to a cardiac diagnosis and/or therapy.

Figure 1:
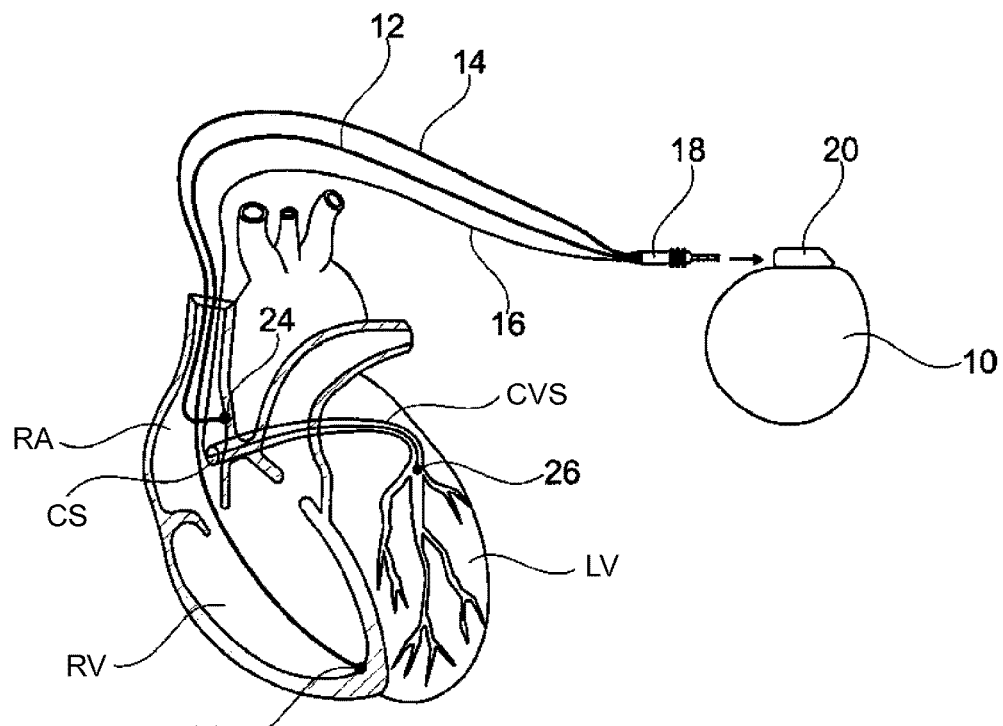
FIG. 1 shows, in a position of implantation, various elements constituting a CRT system according to the prior art.

FIG. 1 shows, in a position of implantation, the different elements of a CRT system according to the prior art.

This system includes a generator 10 of a CRT pacemaker, for example of the Paradym CRT family from Sorin CRM, Clamart, France. This generator is in the form of a housing of a volume of about 30 cm$^3$ to which three leads 12, 14 and 16 are coupled to by a connector 18 inserted into a connector head 20 of the generator 10, typically an IS-4 standard connector. The generator 10 includes a long duration battery for powering internal circuitry of control and of detection/stimulation, the average power consumption of which is of the order of 30 µW.

The leads of the CRT system include an endocardial right ventricular lead 12 introduced into the venous system, including a lead body of a typical diameter of 4 French (1.33 mm), terminated at its distal end by a lead head carrying a detection/stimulation electrode 22 anchored to the bottom of the cavity of the right ventricle RV.

The system may also (optionally) include an endocardial right atrial lead 14 of a structure comparable to that of the lead 12 with a lead body terminated at its distal end by a lead head implanted in the right atrium RA and provided with an atrial detection electrode 24.

For detection/stimulation of the left ventricle, it is not possible, or at least extremely risky, to use an endocardial lead, and for this reason a lead inserted into the coronary venous system via the coronary sinus CS opening in the right ventricle is generally used as a left ventricular lead 16. This coronary lead 16 is provided at its distal end of an electrode 26 positioned in abutment against the wall of the left ventricle LV in order to be able to stimulate the latter in the area of this electrode. Alternatively, the left ventricular lead 16 may be an epicardial lead introduced between the wall of the myocardium and the epicardial bag surrounding the latter, so as to come, in the same method, in contact with the outer wall of the ventricular muscle to be stimulated.

Figure 2:
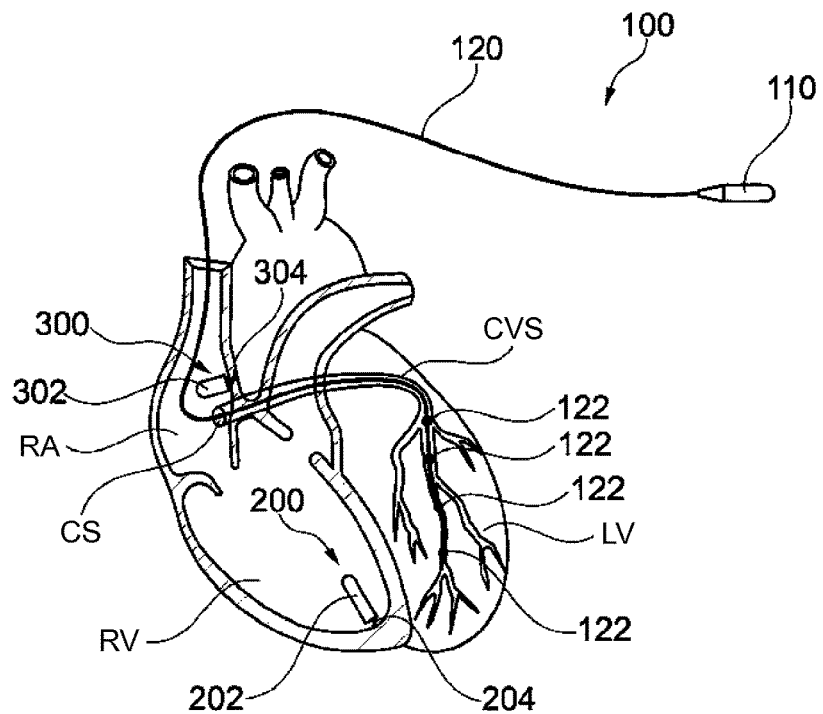
FIG. 2 shows, in a position of implantation, various elements constituting a CRT system according to one embodiment of the invention.

FIG. 2 is homologous to FIG. 1, but for a CRT system 100 according to the invention.

This system includes, instead of the generator 10, a device hereinafter referred to as a "hybrid capsule" 100, associated with a single lead 120 coupled to the body 110 of the hybrid capsule by a simplified, permanent, connection system replacing a connector such as the IS-4 connector 18 of the system according to the prior art shown in FIG. 1. In other words, the lead 120 extends the body 110 of the capsule without solution of continuity due to the absence of the connector.

The lead 120 is a lead of the "microlead" type as described in particular in EP 2719422 A1 (Sorin CRM). This is a lead of very small diameter in its distal part, typically a diameter of less than 1.5 French (0.5 mm), preferably at most 1 French (0.33 mm). This lead is made from at least one microcable itself consisting of an electrically conductive core cable coated with an insulating layer surrounding the core cable and having at least one selectively exposed area formed in the insulation layer to form a detection/stimulation electrode. Various microcable structures are especially described in EP 2581107 A1 (Sorin CRM) to which one can refer for further details. Advantageously, as described in EP 2719422 A1 cited above, a plurality of such microcables are joined together in a strand of microcables, each being electrically independent, so as to obtain a multipolar microlead with a plurality of separately selectable electrodes 122. Such a multipolar microlead allows the implementation of a function called "electric repositioning" consisting of selecting, among a number of points corresponding to a plurality of stimulation electrodes respectively connected to one of the microcable of the lead, ensuring that better efficiency. This selection can be made both at the time of implantation of the lead and subsequently by performing tests at regular intervals to verify that the originally chosen site is always optimal, and possibly to select another otherwise.

The distal, active part of the microlead 120 is implanted in the coronary venous system CVS so that the electrodes 122 are in contact with different areas of the wall of the left ventricle LV. The various electrodes 122 may be formed by a plurality of exposed areas of a monopolar zone (these electrodes being thus all active and electrically connected in parallel), or by different, selectively switchable, electrodes of a multipolar microlead.

The system of the invention further includes a leadless capsule 200 implanted in the right ventricle RV. This capsule is of the leadless type, that is to say, it is devoid of any physical connection to an implantable main device (such as the generator 10 of FIG. 1) or non-implanted device. Such a leadless capsule includes a body 202 provided at one end with an anchoring member 204, a generally axially projecting helical screw extending from the body 202 of the capsule, and intended to penetrate the heart tissue by screwing at the implantation site, in the same method as for conventional screw leads.

EP 2394695 A1 (Sorin CRM) describes such a type of leadless capsule with a screw, as well as an accessory for its implantation in the chosen site, by docking the axial screw, rotary drive of the capsule to permanently attach it to the heart wall where it will be maintained by the anchoring axial screw, and then removal of the accessory, the capsule then remaining freely attached to the heart wall.

The body 202 of such a leadless capsule is usually in a generally cylindrical shape with a length of 20 to 40 mm, an outer diameter of less than 6 mm (2 French, a size imposed by the size of the path through the peripheral venous system), and a volume of about 1 $cm^3$.

The leadless capsule incorporates a low power electronic architecture, typically consuming 5-8 µW, which allows the supply of an energy harvesting system or harvester (described for example in EP 2638930 A1 (Sorin CRM) or EP 2639845 A1 (Sorin CRM)) in lieu of a battery whose lifetime is limited by nature.

In the configuration illustrated FIG. 2, a second leadless capsule 300 of a type similar to the capsule 200 is also disclosed, including a body 302 and methods for anchoring to the heart wall 304, this wall being the one of the right atrium RA so as to collect the atrial depolarization signals.

The capsules 200 and 300 are conventional leadless capsules of a type in itself known, and will not be described further for this reason.

Figure 3:
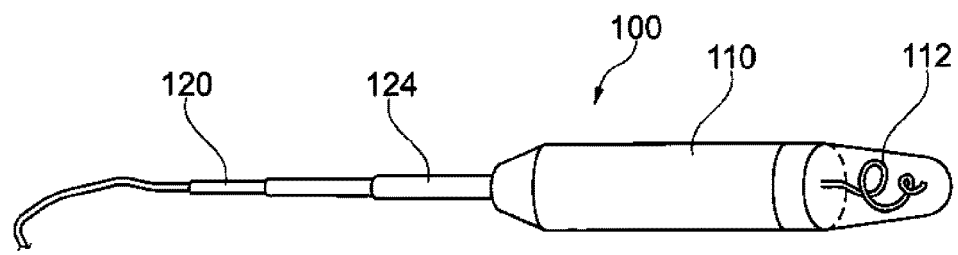
FIG. 3 is an enlarged view of the hybrid capsule of the system of FIG. 2.
Figure 4:
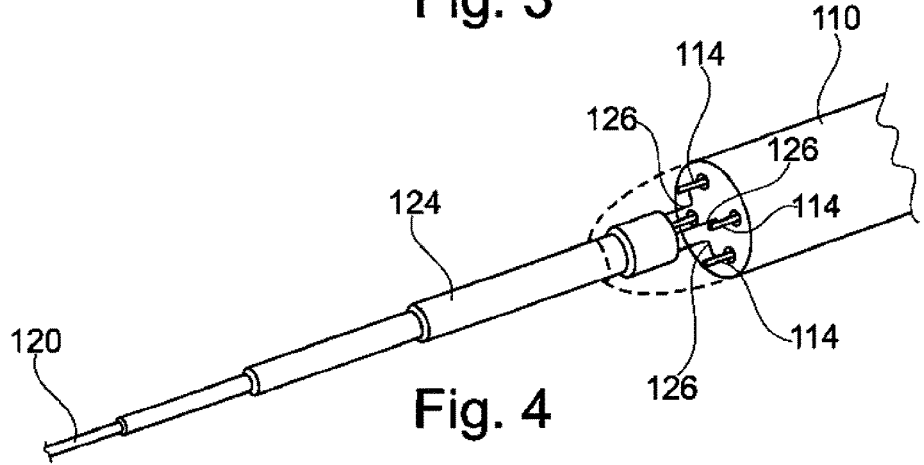
FIG. 4 is a detail showing a method in which the electrical connection of the microlead conductors to the internal circuits of the hybrid capsule is made.

FIGS. 3 and 4 are enlarged views showing details of the hybrid capsule 100 of the system according to the invention.

The hybrid capsule includes a waterproof, biocompatible and atraumatic metal tubular body 110 (made of titanium or alloy). The outer diameter of this body is at most 6 mm (18 French), has a length of at most 40 mm, and its volume is of the order of 1 $cm^3$. In other words, the body of the hybrid capsule 110 has substantially the same dimensions as a conventional leadless capsule such as the capsules 200 and 300.

At one end, the body 110 of the hybrid capsule is provided with an antenna 112 for wireless communication, especially to enable it to communicate with an external device programmer such as a programmer or a remote data transmission device, including RF telemetry in the MICS (Medical Implant Communication Service) band, MEDS, in public trivialized ISM bands used by medical devices, or communication according to Bluetooth protocols.

For Human Body Communication (HBC) between capsules, there may be provided a ring-shaped electrode, electrically insulated from the body 110 of the capsule and from the antenna 112, intended to ensure the transmission of data by contact with the tissues or the blood via electrical pulses in the patient's body.

At the opposite end, the hybrid capsule 110 is extended by the microlead 120, with an intermediate region 124 of transition providing, on a length of the order of 30 mm, a progressive stiffness gradient between the rigid end of the body 110 and the flexible part of the microlead 120.

As shown in FIG. 4, the connection between the microcable 126 of the microlead 120 and the internal circuitry contained in the body of the hybrid capsule 110 is achieved by sealed feedthroughs 114, which are unipolar feedthroughs with a conductive pin welded on a base secured to the body 110 of the hybrid capsule and each connected to a respective microcable 126 of the microlead 120.

As for the leadless capsules 200 and 300, the hybrid capsule 110 includes a low power electronic architecture, typically consuming 5-8 µW, powered by a battery or, alternatively, a harvester system for energy harvesting. Advantageously, the electronic circuit of the hybrid capsule 100 also includes one or more rate responsive sensors, such as a 3D accelerometer, and a thermistor to measure the body temperature (in a configuration wherein the body 110 of the hybrid capsule is subcutaneously implanted).

Figure 5:
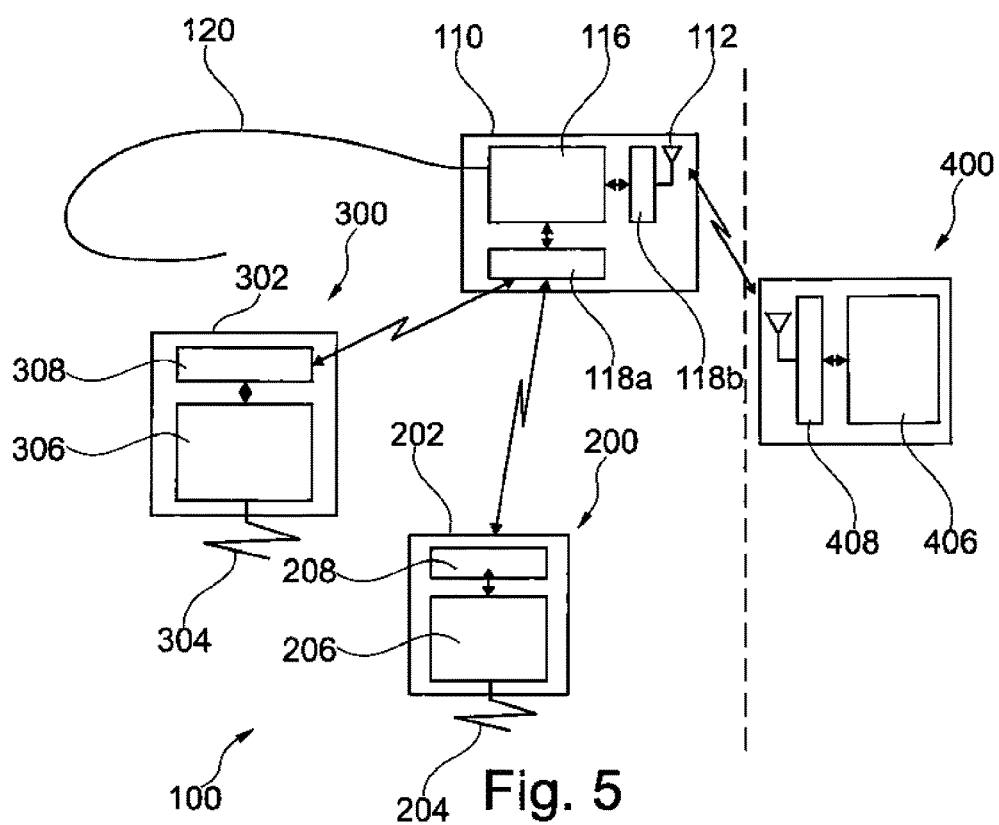
FIG. 5 is a block diagram describing interactions between different elements of a system according to one embodiment of the invention.

FIG. 5 is a block diagram illustrating the interactions between the various devices of the system of the invention.

Each of the hybrid capsule 100 or of the leadless capsules 200 and 300 includes electronic control circuits, respectively 116, 206, 306, coupled to a transmitter/receiver for wireless communication, respectively 118a, 118b, 208 and 308, allowing mutual communication between the different capsules 100, 200, 300 as well as the communication of the hybrid capsule 110 with a remote device 400. The remote device 400 includes circuits 406 coupled to transmitter/receiver 408. The external device 400 may especially be the programmer of a practitioner, the communication being then used to interrogate the implantable system, to read the data stored in memory, change some settings, etc.

The external device 400 can also be a home monitoring device, that is to say, an external device monitoring the patient's condition at home, with possibility of transmitting information to a remote, hospital or other, site. The Smartview Remote Monitoring System from Sorin CRM is an example of such an external device.

Communication between the hybrid capsule 100 and the leadless capsules 200 and 300 (via the respective circuits 118, 208 and 308) is an intracorporeal communication of the HBC (Human Body Communication, intracorporeal communication) type, implementing for example a communication technique by pulses transmitted through the interstitial tissues of the patient's body, these pulses being generated, transmitted, collected and detected by appropriate circuitry such as that described in EP 2441491 A1 (Sorin CRM) and EP 2486953 A1 (Sorin CRM). The communication between the hybrid capsule 110 and the external device 400 is an RF telemetry communication, for example in the MICS, MEDS, ISM bands or using the Bluetooth protocol.

The hybrid capsule 100 acts as a master device or hub in a star wireless network architecture, whose leadless capsules 200 and 300 are slave devices.

Specifically, the role of hybrid capsule 100 (master) is:
To detect activity on the left ventricle, collected on the electrodes of the microlead 120 and galvanically directly transmitted, via the microcables 126 of the microlead;
To stimulate the left ventricle by sending appropriate pulses to the electrodes of the microlead 120;
To receive information from the right ventricular capsule 200 and to the left atrial capsule 300;
To send commands to these right ventricular 200 and left atrial 300 capsules; and
To interact with a device 400 external to the patient's body.

The role (slave) of the right ventricular leadless capsule 200 is:
To detect activity on the right ventricle from the signals detected by the electrode in contact with the myocardium in this area, for example by the anchoring screw 204 if it also serves as an electrode;
To send relevant information to the hybrid capsule 100 located in a subcutaneous region; and
To execute orders sent by the hybrid capsule 100, including the issuance of stimulation pulses to the right ventricle.

The role (slave) of the atrial leadless capsule 300 is:
To detect the atrial activity from the signals detected by the electrode in contact with the myocardium in this zone, for example by the anchoring screw 304 if it also serves as an electrode;
To send corresponding information to the hybrid capsule 100 located in a subcutaneous region; and
To execute orders sent by the hybrid capsule 100, including the issuance of stimulation pulses to the right ventricle.

The invention as described above has a number of advantages, among which are:
Compared to a conventional pacemaker generator, the hybrid capsule 100 according to the invention allows a further miniaturization and a significant reduction of energy consumption. In the invention, a capsule with a body 110 of approximately 1 cm$^3$, associated with a microlead of 1 French (0.33 mm), replaces a generator of 30 cm$^3$ which is connected to a coronary lead of a 4 French diameter (1.33 mm);
Simplification of the system through the complete removal of the connector;
Possibility to use for the implantation a microcatheter such as that described in EP 2682151 A1 (Sorin CRM), which is used to insert a microlead while keeping to traditional implantation accessories (introducer, guidewire, catheter, etc.), which will be used in the same method than before, so with the same surgical procedure;
Saving time for implantation, due to the deletion of the lead connecting step on the pacemaker connector head, and of the lead test step for checking the conformity of the interaction lead/generator;
System compatible by design with magnetic resonance imaging exams (MRI), which are not likely to destroy the electrodes of the system through the use of biocompatible parts in plastic or silicone material and of rigid titanium parts;
Increased reliability with a simplified design and reduced number of parts; and
Possibility of further reducing the diameter of the hybrid capsule below 20 French (6.6 mm), depending on the volume of electronics and of the power supply system.

Many variants of the invention may be envisaged, in particular in configurations wherein the system is adapted to other applications than CRT therapy, or even to another application than cardiac therapy. In particular:
The microlead can be a microlead capable of being inserted into a vein, into an artery, in the lymphatic system, in the nervous system (especially for Vagus Nerve Stimulation (VNS) therapy) and generally throughout any body cavity;
The hybrid capsule may include more leads which extend the body 110 of the capsule itself;
The leadless capsules of the system according to the invention can be adapted for the detection or delivery of therapies not only in the heart, but also to other organs such as the stomach, intestine, lung, brain, etc.; and
The system may include a plurality of hybrid capsules, one of which is the master and the other(s) is(are) the slave(s). These additional hybrid capsules will then functionally play the same role as the leadless capsules, with the difference that the detection/stimulation will be operated by the active distal region of the microlead, of the additional hybrid capsule, instead of being directly operated by the anchoring screw or by the electrode at the contact point with the wall of a leadless capsule.

What is claimed is:
1. A system forming an active implantable medical device comprising:
a subcutaneous autonomous unit, comprising:
a first seal body housing electronic circuitry and power supply means for the electronic circuitry; and at least one lead for detecting and/or delivering therapy extending from said first seal body, such lead comprising at least one electrode; and at least one intracorporeal autonomous leadless capsule suitable for implantation in or against a body and comprising:
a second seal body housing electronic circuitry and power supply means for these circuits;
anchoring means coupled to a wall of said second seal body; and
at least one electrode suitable for coming into direct contact with said second seal body, in which the subcutaneous autonomous unit and the leadless capsule each include transmitter/receiver means for intracorporeal mutual wireless communication, the subcutaneous autonomous unit operating as master and the leadless capsules operating as slaves under the control of the subcutaneous autonomous unit, and wherein the subcutaneous autonomous unit further comprises:
centralization means of the data transmitted by the leadless capsules, and
means of communication with the outside, able to operate a remote transmission, to a remote device, of the data collected by the means of centralization of data, wherein the at least one detection and/or therapy delivery lead is a microlead comprising at least one microcable formed of an electrically conductive core cable connected to one pole of said electronic circuits, with an insulation layer surrounding the core cable and comprising at least a selectively exposed area formed in the insulation layer and for forming said electrode for detection and/or therapy delivery, the diameter of the microlead being at most 1 French (0.33 mm) in its distal region comprising said selectively exposed area; and wherein the subcutaenous autonomous unit is a hybrid capsule whose volume is at most 1 cm$^3$ and wherein:
the microlead is directly connected to the electronic circuits of the hybrid capsule,
the at least one microlead extends said first seal body on one side thereof, and
the core cable of the microcable, or of each microcable, is directly connected to a respective pole of the electronic circuits of the hybrid capsule.

2. The system of claim 1, wherein the hybrid capsule is devoid of means for anchoring to a wall of an organ.

3. The system of claim 1, wherein the seal body of the hybrid capsule is a metal body comprising at least one hermetic and electrically insulating bushing for passage of the connection of the core cable of the microcable, or of each core cable of each microcable, to the respective pole of the electronic circuits contained in the body of the hybrid capsule.

4. The system of claim 1, wherein the body of the hybrid capsule supports, at the side opposite to the side closed by the microlead, an antenna for transmitting/receiving wireless communication with said remote device.

5. The system of claim 1, wherein the at least one microlead for detection and/or therapy delivery comprises, in the proximal region of the microlead attached to the body of the hybrid capsule, a transition zone with variable stiffness gradient, decreasing in the distal direction.

6. An active implantable medical device, comprising:
an implantable master unit with a volume of at most 1 cm$^3$, comprising:
a body housing a circuit and a power supply;
a microlead extending from the body, wherein the microlead is directly connected to the circuit, the microlead including a microcable directly connected to a pole of the circuit, wherein the diameter of the microlead is at most 1 French (0.33 mm) in a distal region;
a transmitter and a receiver for wireless communication; and
a memory; and
an implantable leadless capsule, comprising:
a body housing a circuit and a power supply;
an anchor configured to be coupled to a wall of an organ;
an electrode; and
a transmitter and a receiver for wireless communication with the master unit.

7. The active implantable medical device of claim 6, wherein the master unit does not include any mechanism for anchoring the body to a wall of an organ.

8. The active implantable medical device of claim 6, wherein the body of the master unit is a metal body comprising a hermetic and electrically insulating bushing for passage of a core cable of the microcable to the respective pole of the circuit.

9. The active implantable medical device of claim 6, wherein the master unit further comprises an antenna for wirelessly communicating with a remote device.

10. The active implantable medical device of claim 9, wherein the remote device is located outside of a patient and the antenna is used to transmit data collected from the leadless capsule and stored in the memory.

11. The active implantable medical device of claim 6, wherein the microlead comprises, in a region proximate to the body of the master unit, a transition zone with variable stiffness gradient, decreasing in a distal direction.

12. The active implantable medical device of claim 6, wherein the master unit is configured to operate as a master device and the leadless capsule is configured to operate as a slave device under the control of the master unit.

13. The active implantable medical device of claim 12, further comprising a second implantable leadless capsule, the second implantable leadless capsule including a transmitter and a receiver for wireless communication with the master unit.

14. The active implantable medical device of claim 13, wherein the second implantable leadless capsule is configured to operate as a slave device under the control of the master unit.

15. The active implantable medical device of claim 6, wherein the microcable includes an insulation layer surrounding a core cable, the insulation layer including a selectively exposed area for forming an electrode for at least one of detection or therapy delivery.

16. The active implantable medical device of claim 6, wherein the master unit is a hybrid capsule.

17. The active implantable medical device of claim 16, wherein the hybrid capsule does not include a separate electrical connector between the microlead and the hybrid capsule.

18. The active implantable medical device of claim 17, wherein the microlead further includes a second microcable and wherein the second microcable is directly connected to a second pole of the circuit.

19. The active implantable medical device of claim 6, wherein the diameter of the hybrid capsule is at most 20 French (6.6 mm).

\* \* \* \* \*